United States Patent
Henry

(10) Patent No.: US 12,403,041 B2
(45) Date of Patent: Sep. 2, 2025

(54) COORDINATED DICHOTIC SOUND COMPRESSION

(71) Applicant: 3M INNOVATIVE PROPERTIES COMPANY, St. Paul, MN (US)

(72) Inventor: Paul D. Henry, Carmel, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 211 days.

(21) Appl. No.: 17/756,964

(22) PCT Filed: Dec. 7, 2020

(86) PCT No.: PCT/IB2020/061604
§ 371 (c)(1),
(2) Date: Jun. 7, 2022

(87) PCT Pub. No.: WO2021/116886
PCT Pub. Date: Jun. 17, 2021

(65) Prior Publication Data
US 2023/0051367 A1 Feb. 16, 2023

Related U.S. Application Data

(60) Provisional application No. 62/947,115, filed on Dec. 12, 2019.

(51) Int. Cl.
*A61F 11/08* (2006.01)
*A61F 11/14* (2006.01)
(Continued)

(52) U.S. Cl.
CPC ............ *A61F 11/08* (2013.01); *A61F 11/145* (2022.01); *G10K 11/17823* (2018.01);
(Continued)

(58) Field of Classification Search
CPC .......... A61F 11/08; A61F 11/145; H04R 1/10; H04R 1/1083; H04R 25/50; H04R 25/552;
(Continued)

(56) References Cited

U.S. PATENT DOCUMENTS 3,509,289 A 4/1970 Briskey et al.
4,677,678 A 6/1987 McCutchen
(Continued)

FOREIGN PATENT DOCUMENTS

EP 1674061 A1 6/2006
EP 3337186 A1 6/2018
(Continued)

OTHER PUBLICATIONS

International Search Report for PCT International Application No. PCT/IB2020/061604, mailed on Mar. 4, 2021, 5 pages.

*Primary Examiner* — Carolyn R Edwards
*Assistant Examiner* — Kuassi A Ganmavo
(74) *Attorney, Agent, or Firm* — Katherine Scholz; Jonathan V. Sry

(57) ABSTRACT

An in-ear hearing protection device is provided. The in-ear hearing protection device includes a microphone (410) configured to receive an ambient sound. The in-ear hearing protection device also includes a processor (420) configured to perform an attenuation function on the received ambient sound to provide an attenuated sound. The in-ear hearing protection device also includes a speaker (440) configured to broadcast the attenuated sound. The in-ear hearing protection device also includes a communication module (430) configured to receive a second attenuation function detail from a second in-ear protection device. The processor is configured to calculate a first attenuation function detail and compare the first and second attenuation function details.

(Continued)

The performed attenuation function is based on one of the first and second attenuation function details.

17 Claims, 10 Drawing Sheets

(51) Int. Cl.
  *G10K 11/178* (2006.01)
  *H04R 1/10* (2006.01)
  *H04R 25/00* (2006.01)
(52) U.S. Cl.
  CPC .............. *H04R 1/10* (2013.01); *H04R 1/1016* (2013.01); *H04R 1/1083* (2013.01); *H04R 25/50* (2013.01); *H04R 25/552* (2013.01); *H04R 2201/107* (2013.01); *H04R 2460/01* (2013.01)
(58) Field of Classification Search
  CPC .............. H04R 1/1016; H04R 2460/01; H04R 2201/107; G10K 11/05; G10K 11/17823
  See application file for complete search history.

(56) References Cited

U.S. PATENT DOCUMENTS

| | | | |
|---|---|---|---|
| 9,014,406 B2 | 4/2015 | Thomsen et al. | |
| 9,288,587 B2 | 3/2016 | Ma | |
| 9,742,471 B1* | 8/2017 | Thoen .................... | H04W 4/80 |
| 2004/0190734 A1* | 9/2004 | Kates ................... | H04R 25/552 |
| | | | 381/106 |
| 2006/0140416 A1* | 6/2006 | Berg ....................... | A61F 11/12 |
| | | | 381/72 |
| 2006/0233385 A1* | 10/2006 | Allegro Baumann ...................... | |
| | | | H04R 25/552 |
| | | | 381/60 |
| 2010/0177906 A1* | 7/2010 | Vetterli ................ | A61B 5/7257 |
| | | | 381/74 |
| 2011/0274284 A1* | 11/2011 | Mulder ............ | G10K 11/17873 |
| | | | 381/72 |
| 2014/0003636 A1* | 1/2014 | Bodvarsson ........... | H04R 5/033 |
| | | | 381/311 |
| 2014/0044269 A1* | 2/2014 | Anderson ........... | H04R 1/1083 |
| | | | 381/57 |
| 2014/0093090 A1* | 4/2014 | Bajic ....................... | H04R 3/04 |
| | | | 381/74 |
| 2015/0249892 A1* | 9/2015 | Kuhnel ................ | H04R 25/407 |
| | | | 381/315 |
| 2015/0319543 A1* | 11/2015 | Xia ..................... | H04R 25/356 |
| | | | 381/321 |
| 2016/0142838 A1* | 5/2016 | Thomsen ............. | H04R 25/505 |
| | | | 381/314 |
| 2016/0227332 A1* | 8/2016 | Pedersen ............... | H04R 25/558 |
| 2018/0295456 A1* | 10/2018 | Bramsløw ........... | H04R 25/552 |
| 2020/0178005 A1* | 6/2020 | Longaa ................. | H04R 25/30 |
| 2020/0202889 A1* | 6/2020 | Piechowiak ......... | H04R 25/407 |
| 2020/0314562 A1* | 10/2020 | Pedersen ............. | H04R 1/1083 |

FOREIGN PATENT DOCUMENTS

| | | |
|---|---|---|
| WO | 1999043185 A1 | 8/1999 |
| WO | 2004114722 A1 | 12/2004 |

* cited by examiner

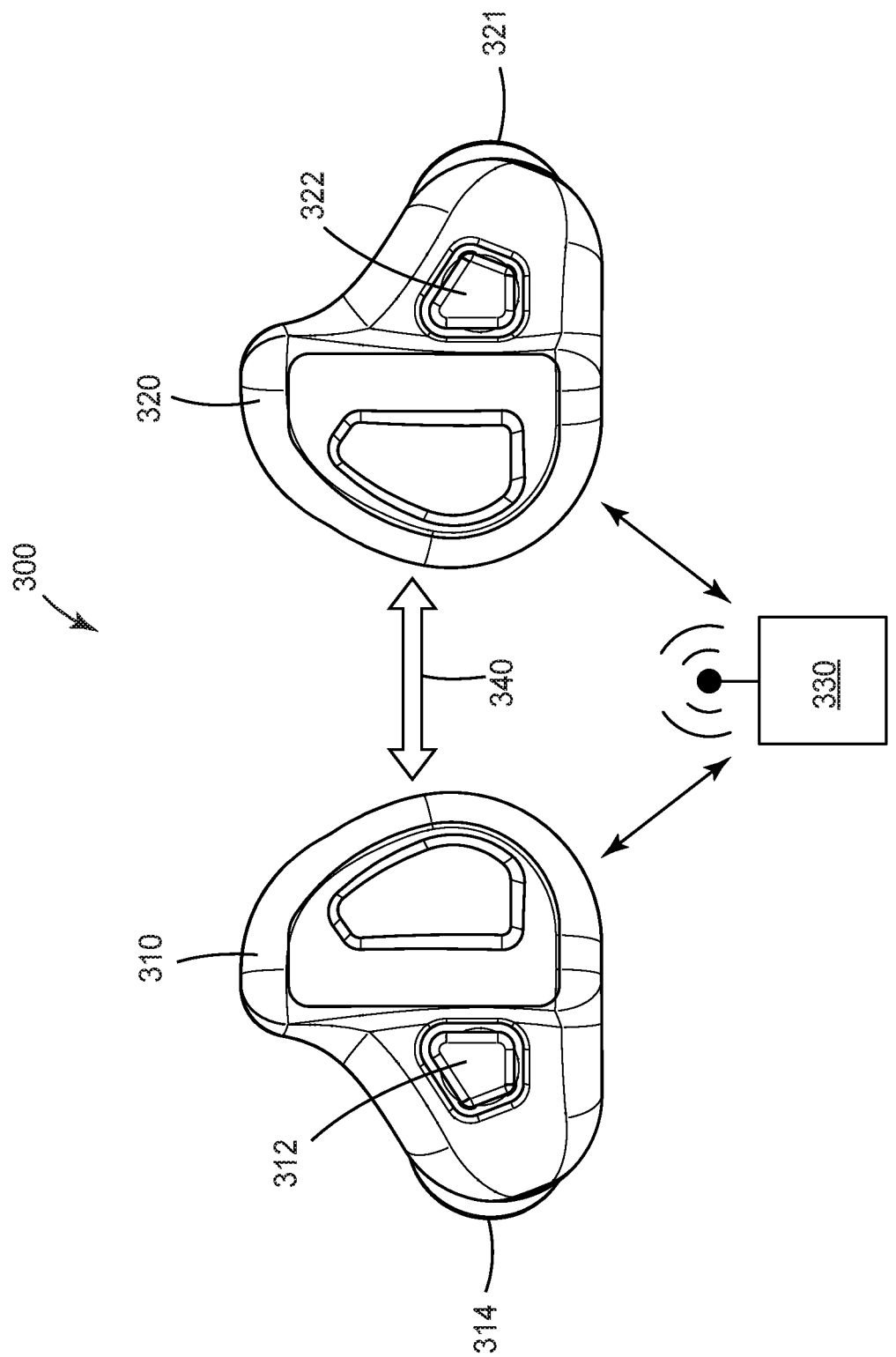

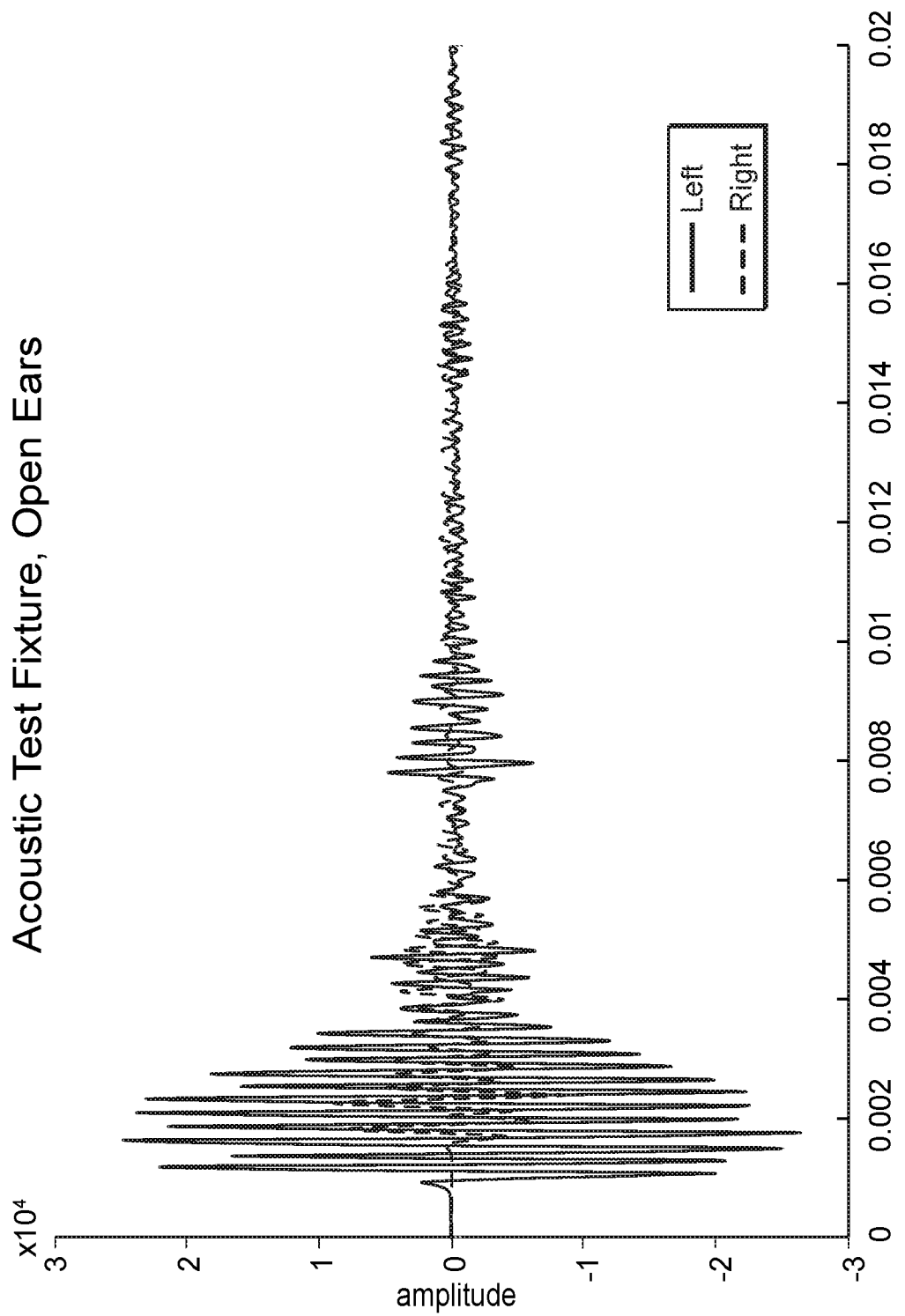

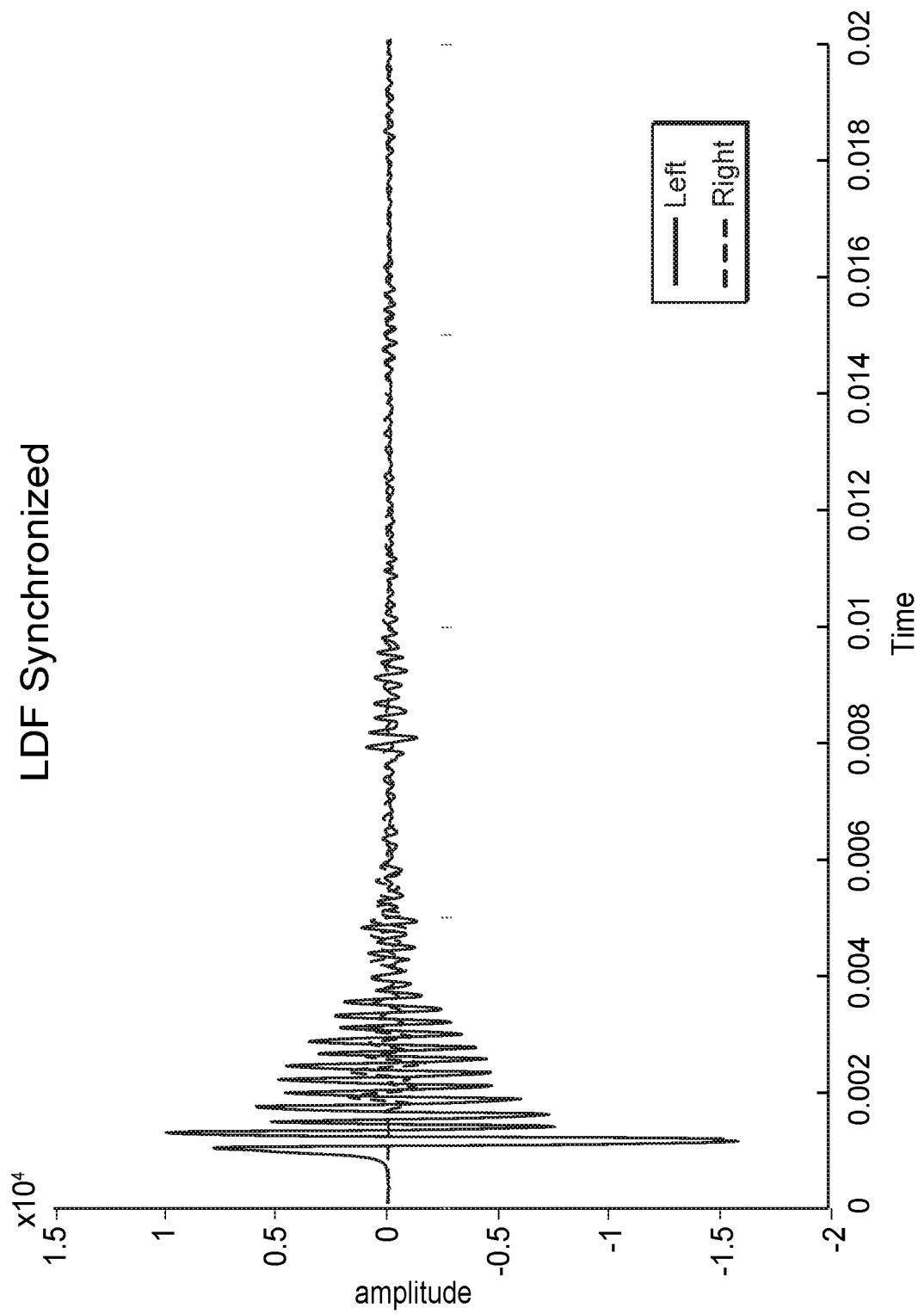

COORDINATED DICHOTIC SOUND COMPRESSION

CROSS REFERENCE TO RELATED APPLICATIONS

This application is a national stage filing under 35 U.S.C. 371 of PCT/IB2020/061604, filed Dec. 7, 2020, which claims the benefit of U.S. Provisional Application No. 62/947,115, filed Dec. 12, 2019, the disclosure of which is incorporated by reference in its/their entirety herein.

BACKGROUND

There are two main types of hearing protectors—those intended for wearing over the ear and those intended for wearing within the ear. Some hearing protectors passively reduce sound entering a user's ear, using a sound blocking material. Others have additional electronic circuitry to actively process ambient sound to safe levels.

BRIEF DESCRIPTION OF THE DRAWINGS

FIG. 3 illustrates a pair of in-ear hearing protection devices in accordance with an embodiment of the present invention.

FIGS. 7A-C illustrate responses discussed in detail in the Examples.

DETAILED DESCRIPTION

Passive hearing protection can be as simple as an expanding foam article intended for placement within a user's ear. Or passive hearing protection can include ear muffs configured for placement over the ear. However, passive hearing protection limits the ability of a user to hear their surroundings. In some scenarios, it may be necessary for a user to hear sound at safe levels nearby, for example voices, footsteps or environmental warning sounds.

Active hearing protection includes one or more microphones that receive ambient sound from a user's surroundings and uses one or more speakers to reproduce it at a safe level. Active hearing protection devices use electronic circuitry to pick up ambient sound through the microphone and convert them to safe levels before playing it back to the user through a speaker. Additionally, active hearing protection may comprise filtering or cancelling of undesired sound content, for example actively reducing the sound of a gunshot while providing human speech at substantially unchanged levels. Active hearing protection can include in-ear protection as well as over-ear protection.

Some active hearing protection units are level dependent, such that an electronic circuit adapts the sound pressure level. Level dependent hearing protection units help to filter out impulse noises, such as gunshots from surrounding noises, and/or continuously adapt all ambient sound received to an appropriate level before it is reproduced to a user. Active hearing protection units, specifically level dependent active hearing protection units, may be necessary to facilitate communication in noisy environments, or environments where noise levels can vary significantly, or where high impulse sounds may cause hearing damage. A user may need to hear nearby ambient sounds, such as machine sounds or speech, while also being protected from harmful noise levels. Active hearing protection can also be used to increase environmental awareness by amplifying soft sounds.

Figure 1:
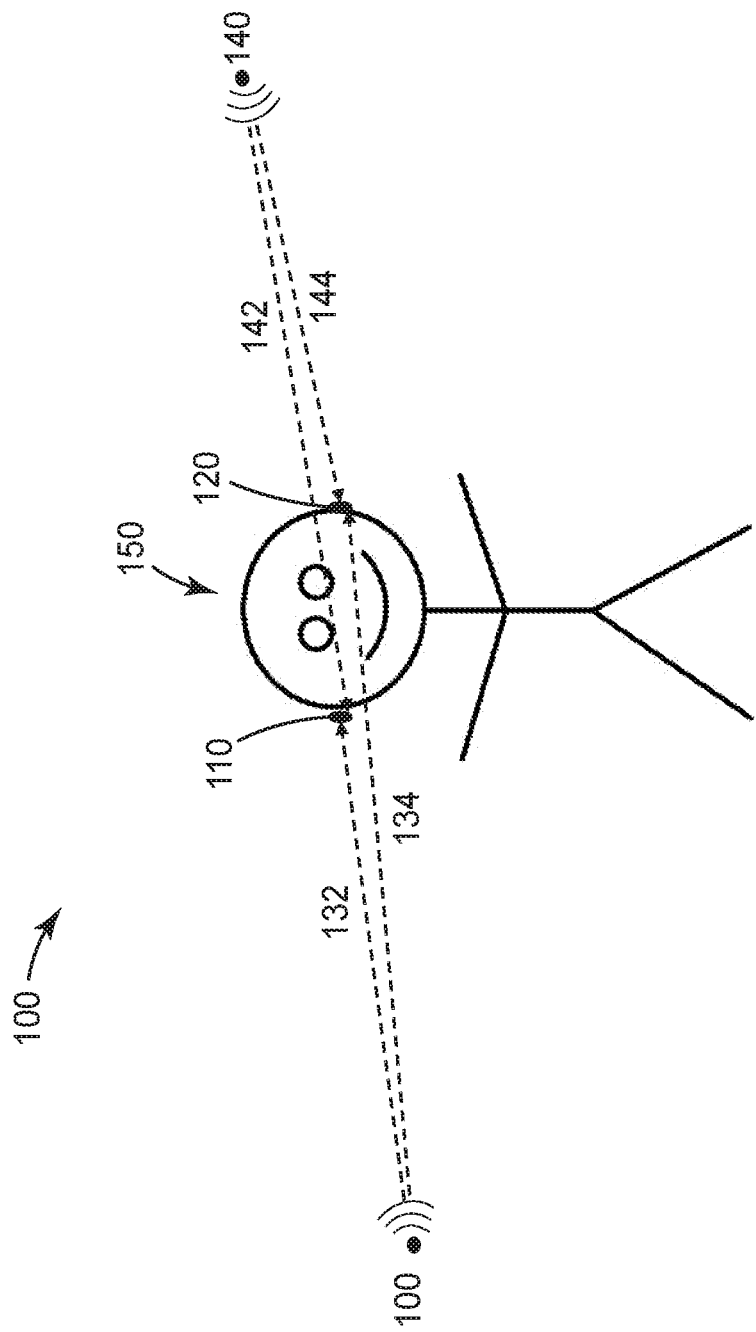
FIG. 1 illustrates an example environment in which embodiments of the present invention may be useful.

FIG. 1 illustrates an example environment in which embodiments of the present invention may be useful. Environment 100 illustrates an individual 150 wearing a pair of in-ear protection devices 110, 120. Each of in-ear protection devices 110, 120 operate independently. First, a sound signal is received by a microphone in an active hearing protection unit. The received sound signal is converted to an electronic signal for processing. After processing the sound signal such that all frequencies are at safe levels, the sound signal is reproduced and played back to a user through a speaker.

However, each of a first sound 130 and a second sound 140, may be received and processed differently by each of in-ear protection devices 110 and 120. For example, sound 130 travels a distance 132 to protection device 110 and a different distance 134 to protection device 120. Additionally, distance 132 is direct to device 110, while distance 134 may require the sound travel around the head of user 150. The differences in distances and obstructions between paths 132 and 134 may cause devices 110 and 120 to treat a received sound differently. Similarly, for sound 140, a travel path to a first protection device 110 is longer than a travel path to second protection device 144.

The human ears, in addition to picking up sound and providing it to the brain for processing, are also important for determining the direction from where a sound is coming from. The ability to localize sounds 130 and 140 may be important for the safety of user 150. For example, it may be important for user 150 to perceive that sound 140 is coming from a higher altitude than sound 130. Additionally, while FIG. 1 illustrates a two-dimensional schematic of an environment, in a true 3-dimensional environment the importance increases. When a perceived sound indicates a safety threat, it is important for a user to be able to accurately determine where it comes from. Generally, an individual 150 localizes a sound by comparing the different volumes of that sound in each ear, commonly know as interaural level difference, or ILD However, because each of hearing protection devices 110 and 120 operate independently, it is possible, and common in practice, that each applies a different compression to received sounds 130 and 140, resulting in inconsistent volumes being presented to a user. In addition to disrupting the natural localization process, the inconsistencies can also cause vertigo in some users, distortion, and latency in signal processing.

Figure 2B:
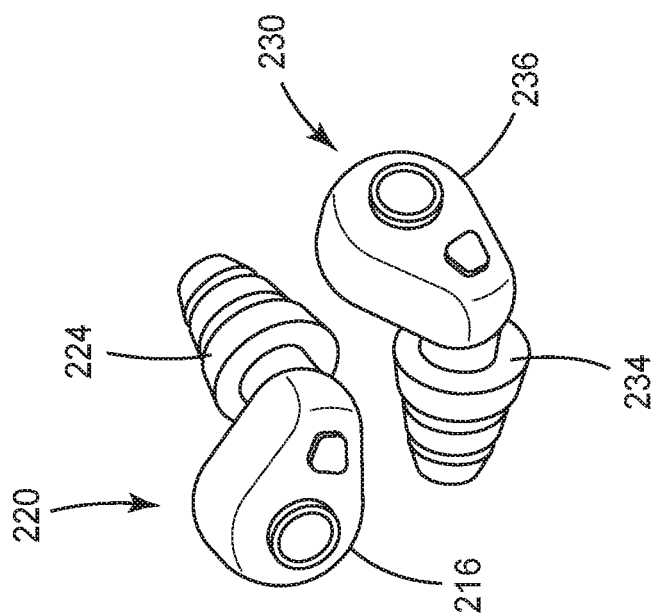
FIGS. 2A and 2B illustrate protective hearing devices.
Figure 2A:
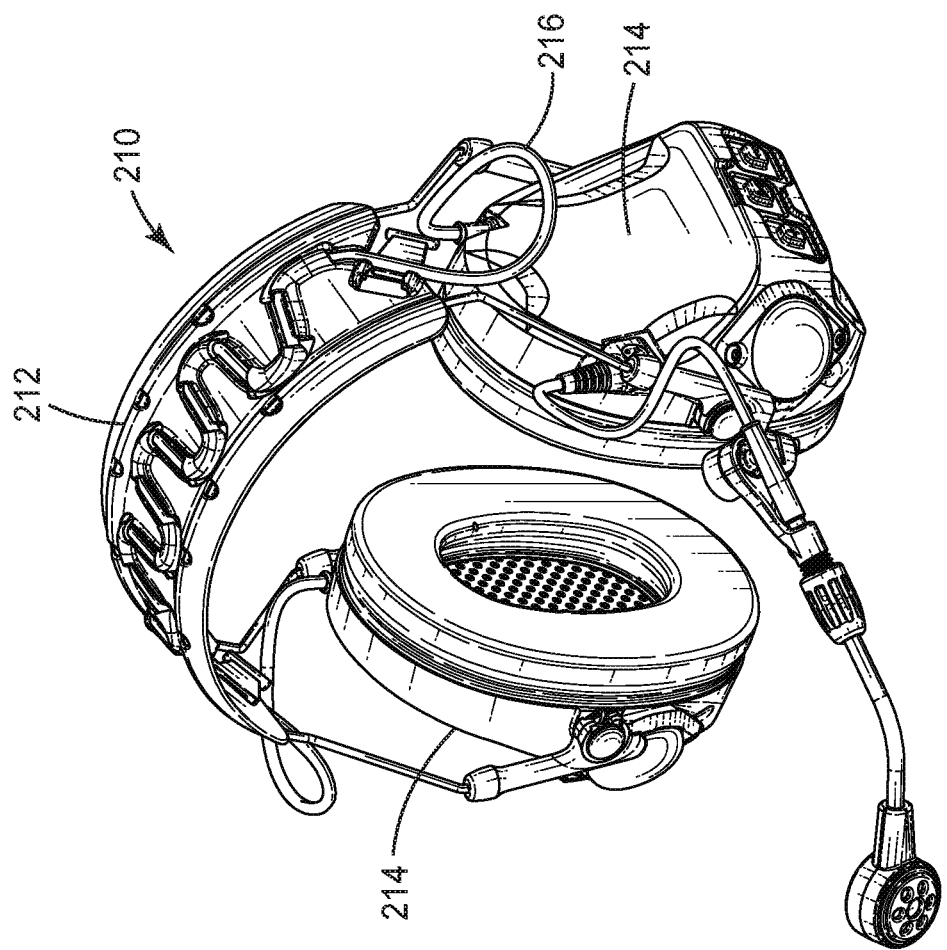

FIGS. 2A and 2B illustrate protective hearing devices. Over-the ear protection system 210 includes two earmuffs 214, each with a microphone (not shown) configured to pick up sound, and a speaker (not shown) configured to deliver attenuated sound to a user wearing system 210. In-ear protection devices 220 and 230 are each configured to be placed inside a user's ear. Each of in-ear protection devices 220, 230 includes a microphone 224, 234, respectively, and a speaker 226, 236, respectively.

Because over-the-ear headsets are larger, there is more room inside each earmuff 214 for a power source and communication module. Additionally, because an over-thehead band 212 is commonly used to position headset 210 on a user's head, it can be used to keep a wired cable 216 in place, allowing for a wired connection between each of earmuffs 214. Connecting the processors in each of earmuffs 214 allows for coordination of compression, reducing distortion and discomfort.

In contrast, a wired solution is not preferred for in-ear protection devices, as wires can get tangled. Additionally, while a wired solution could potentially allow for continuous communication between in-ear protection device 220 and 230, it does not address the power consumption concern.

In-ear protection devices 220, 230 can communicate using a wireless network. However, because the entire device 220, 230 is configured to fit within a user's ear, the wireless communication module must be small. Additionally, communication modules require their own power source as well.

A system is needed that allows for a pair of in-ear protection devices to communicate and coordinate compression of sound. The system must allow for communication between each of a pair of in-ear protection devices, and also be sensitive to power consumption. The two in-ear protection devices should be able to send sound pressure, compression level, and attenuation information between the two in-ear protection devices.

FIG. 3 illustrates a pair of in-ear hearing protection devices in accordance with an embodiment of the present invention. A hearing protection system 300 includes a first earpiece 310 and a second earpiece 320. In the illustrated embodiment, earpiece 310 is intended for insertion into a user's left ear, while earpiece 320 is intended for insertion into a user's right hear. In another embodiment, earpieces 310, 320 are not specific to a left or right ear of a user. Earpiece 310 includes a microphone 312 configured to receive ambient sound for processing, and a speaker 314 configured to provide processed sound to a user's ear. Earpiece 320 includes a microphone 322 configured to receive ambient sound for processing and a speaker 324 configured to provide processed sound to a user's ear.

Earpiece 310 and earpiece 320 can communicate directly using a wireless datalink 340. Wireless datalink 340 may allow for transmission of small amounts of data, at a useful frequency, without significant power drain. Generally, power consumption is inversely proportional to the refresh rate of data transfer. Therefore, while each of earpieces 310, 320 may be able to sample ambient audio at a rate of at least 16,000 samples per second, data concerning compression and sound attenuation may be transmitted significantly less frequently while still resulting in a reduction in distortion and improved localization for a user. In one embodiment, data transfer occurs between earpieces 310, 320 at a rate of once every 20 milliseconds.

In one embodiment, in-ear hearing protection devices 310, 320 are part of a network with at least one other device 330, as illustrated in FIG. 3. Device 330 may, for example, be a controller configured to provide a network that devices 310, 320 join. Additionally, in some embodiments, wireless datalink 340 does not allow for direct communication between earpieces 310, 320, but routes communication through device 330. Device 330 may also comprise a controller, in one embodiment, that controls activities of one or more devices on the network. For example, device 330 may instruct devices 310, 320 to share attenuation function data, in one embodiment.

In one embodiment, at least one of earpieces 310, 320 is periodically sending attenuation information to the other earpiece, 320, 310. In at least some embodiments, wireless data link facilitates two-way communication, such that earpiece 310 sends attenuation information to earpiece 320, and earpiece 320 sends attenuation information to 310. Periodically sending information may refer to a data transfer rate of at least about once per second, or at least about 5 times per second, or at least about 10 times per second, or at least about 20 times per second, or at least about 50 times per second, or at least about 100 times per second, or at least about 500 times per second, or at least 1000 times per second, or even more frequently. Periodically sending attenuation information allows for continuous coordination of sound compression between earpieces 310, 320, allowing for a more natural sound experience for a user of in-ear hearing protection system 300.

The wireless datalink is achieved using a near field magnetic induction (NFMI) communication system. In one embodiment, the wireless datalink can be maintained between earpieces 310, 320 at a distance up to 1 meter apart. In one embodiment, each earpiece 310, 320 is joined to a communication network, and can communicate with each other and with other devices on the network. NFMI may be used to transmit speech, or other sound, between devices on the network, for example to or from one of earpieces 310, 320. In one embodiment the network may support up to four audio streams while still allowing for transmission of compression-related attenuation information between earpieces 310, 320.

In one embodiment, a control unit 330 is configured to detect both first and second hearing protection systems 310, 320 and provide the command to enter a coordination mode. In one embodiment, the coordination mode is a dichotic mode, such that left and right earpieces 310, 320 simultaneously transmit compression information using wireless data link 340. However, non-simultaneous, and near-simultaneous transmission may also be possible. However, while control unit 330 is illustrated as a separate device for clarity, it is contemplated that either earpieces 310, 320 could comprise the control unit, such that one system sends the command to the other system.

Figure 4:
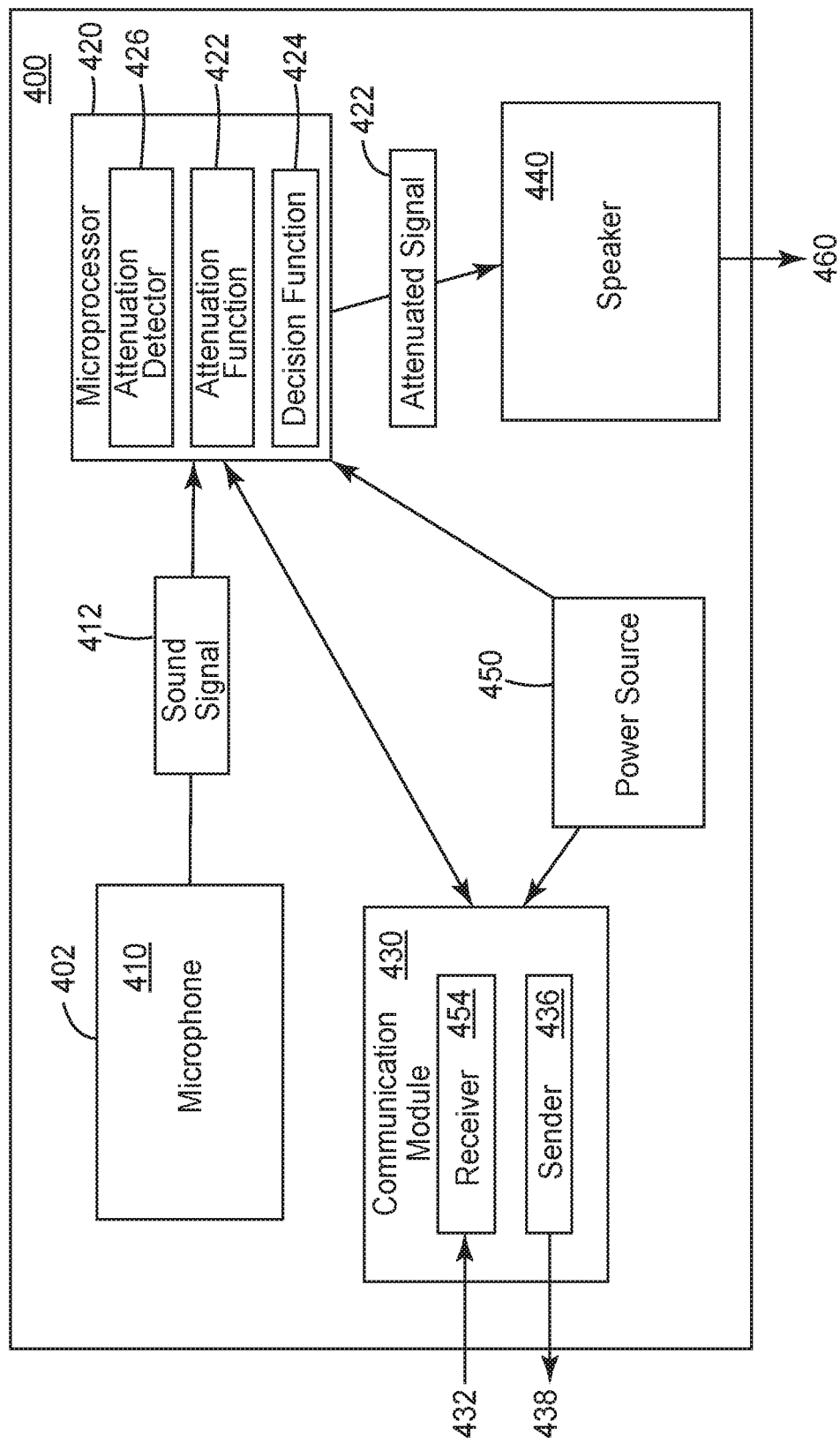
FIG. 4 illustrates an example in-ear hearing protection system in accordance with an embodiment of the present invention.

FIG. 4 illustrates an example in-ear hearing protection system in accordance with an embodiment of the present invention. System 400 illustrates a single earpiece, such as, for example, earpiece 310 or 320 of FIG. 3. However, system 400 may also correspond to a different earpiece design than those illustrated in FIGS. 2 and 3.

Sound 402 is received by microphone 410. Microphone 410 may provide the sound to a processor 420 as a sound signal 412. Sound signal 412 may be either an audio signal, in one embodiment, or converted to an electronic signal, in another embodiment. When operating as an independent hearing protection device, earpiece 400 then applies an attenuation function 422, such as compression, based on attenuation parameters detected by an attenuation detector 426. For example, attenuation detector 426 may detect a sound pressure and determine an amount of compression and other attenuation functions that should be performed before the attenuated signal 422 is provided to speaker 440. Attenuated signal 422 may be an electronic signal or may be converted back to a sound signal. Speaker 440 provides sound 460 to an inner ear of a user wearing earpiece 400.

Communication module 430 of earpiece 400 is configured to facilitate communication and coordinated attenuation of sound for a pair of earpieces 400. Once attributes of sound signal 412 are received by attenuation detector 426, and an attenuation function is prepared, the attenuation function details 438 are provided by sender 436 to another earpiece with which coordinated attenuation is desired. Periodically, attenuation function details 432 are also received from the other earpiece as well. In some embodiments, communication module 430 operates such that attenuation function details 432 are received, and attenuation function details 438 are sent simultaneously. However, in some embodiments the sending and receiving occur non-simultaneously. Additionally, in some embodiments, the frequency of receiving attenuation function details 432 differs from the frequency at which attenuation function details 438 are sent. Additionally, in one embodiment, only one of a pair of earpieces sends details, such that the other of the pair of earpieces modifies its attenuation parameters based on the received details.

When earpiece 400 is in a coordinated mode, after attenuation function 422 is prepared, but before it is applied to sound signal 412, a decision function 424 compares calculated attenuation function details 438 with received attenuation function details 432, and selects one of the two to apply. A similar decision function 424 operates in a coordinated earpiece, such that both a left and a right earpiece apply the same attenuation functionality. For example, in one embodiment, the decision function 424 may consistently select the lowest compression value between a compression value included in details 432 and 438. In another embodiment, it may select the highest compression value. Decision function 424 may also select between equalization criteria included in details 432, 438, in one embodiment, and/or between volume control parameters included in details 432, 438.

A frequency at which communication module 430 sends information to, and receives information from, a paired earpiece may depend on power source 450. For example, more frequent communication will make sound 460 more natural to a user, but will also deplete power source 450 more quickly. Additionally, the frequency may depend on a remaining battery life. For example, frequency of communication may decrease as a battery life drops below a certain threshold. In one embodiment, communication module sends and receives information 432, 438 at least about once per second, or at least about 5 times per second, or at least about 10 times per second, or at least about 25 times per second, or at least about 50 times per second.

Power source 450 needs to fit completely inside earpiece 400, and provide power to communication module 430, speaker 440, processor 420, and microphone 410. Sufficient power needs to be provided to all components for the life of the earpiece. It is important that earpiece 400 have a sufficient use life for a potential user, as failure could cause hearing damage as well as cause a user to potentially stop being able to hear communication from others nearby. In one embodiment, the earpiece is rechargeable, such that the entire earpiece is returned to a charging station when the battery is depleted.

In one embodiment, processor 420 is a microprocessor. In one embodiment, microprocessor 420 also provides compression functionality. The compressor has a 1 ms attack time and a 500 ms release time, in one embodiment. However, the release time may be shorter, depending on power limitations.

Figure 5:
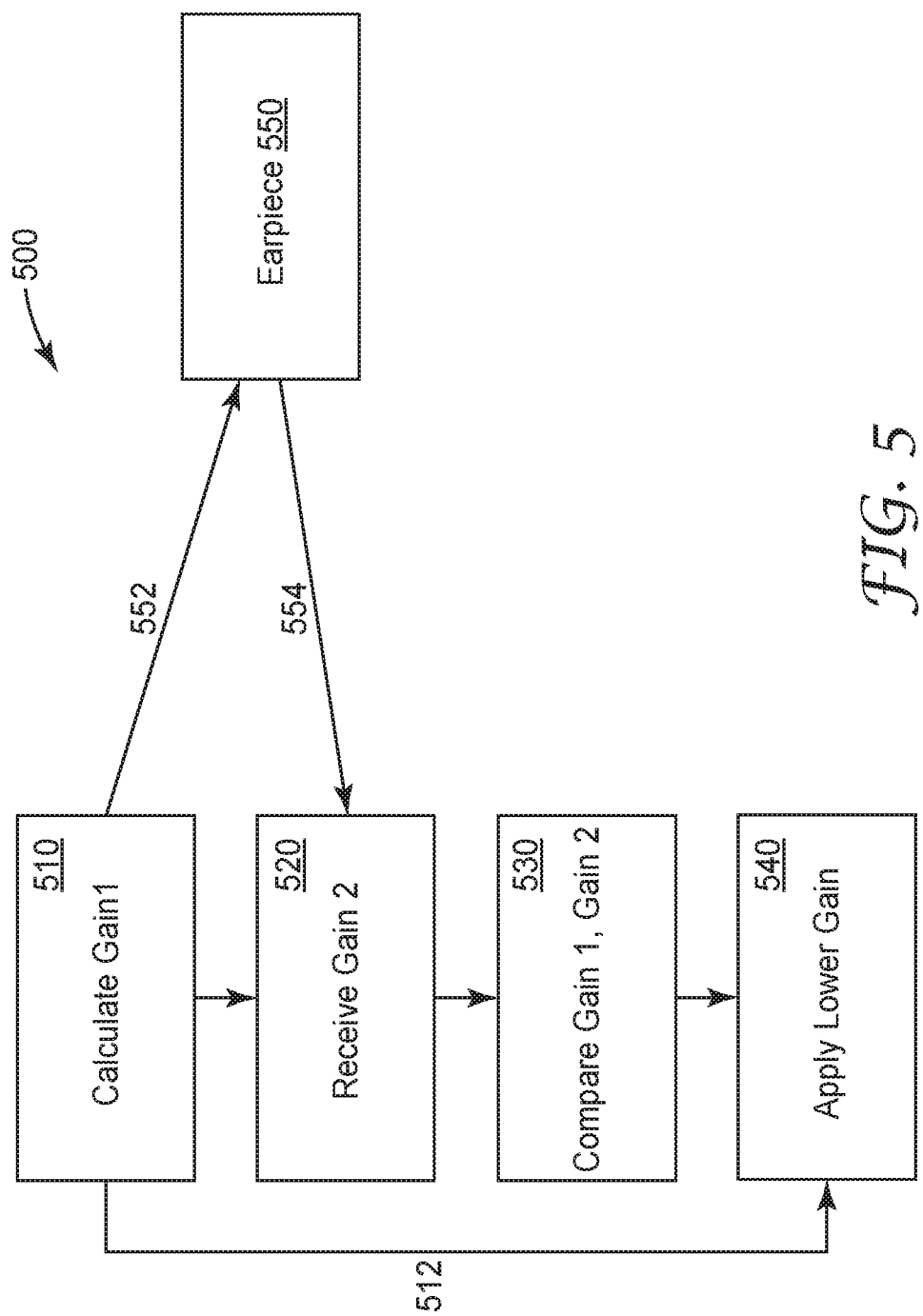
FIG. 5 illustrates a method for coordinating sound compression in accordance with an embodiment of the present invention.

FIG. 5 illustrates a method for coordinating sound compression in accordance with an embodiment of the present invention. Method 500 illustrates one method 500 that may proceed in parallel in an earpiece 550, in one embodiment. However, in another embodiment, method 500 operates independently from any method conducted by earpiece 550. However, while method 500 is described as proceeding in parallel in each earpiece, it is expressly contemplated that other configurations are possible. For example, method 500 may proceed in parallel for two earpieces that are each configured to operate independently. It is also contemplated that, in another embodiment, only one earpiece calculates a gain that both earpieces will apply. Additionally, it is also contemplated that a separate device, such as a controller, may calculate a gain to apply that is provided to both an earpiece performing method 500 and earpiece 550.

Method 500 is described with respect to a gain calculation that takes place in a hearing protection device. However, method 500 may also apply to other attenuation parameters, such as equalization and volume control. These, as well as other suitable parameters, may also be the subject of method 500.

In method 500, in response to receiving a sound signal, a gain is calculated, as illustrated in step 510. When an earpiece operates independently, or no other calculated gain is available, the gain calculated in step 510 is applied, as indicated by arrow 512.

In step 520, a calculated gain is received from another source, as indicated by arrow 554. In one embodiment, the calculated gain is received from earpiece 550. The gain may be transmitted wirelessly from earpiece 550, in one embodiment. In another embodiment, the gain received in step 520 is received from a controller separate from earpieces 500 and 550. The gain may be transmitted using NFMI technology, or another suitable wireless technology.

In block 530, the gain calculated by an earpiece is compared with the gain received from earpiece 550. The comparison may be conducted by a processor located within the earpiece. In another embodiment, the comparison is conducted by a separate device from the earpiece. For example, the comparison may be conducted by earpiece 550, and the earpiece performing method 500 may just apply a gain provided by earpiece 550. Alternatively, the comparison may be done by a separate controller, that determines a lowest gain and provides it to both earpieces.

In block 540, a selected gain is applied. In one embodiment, the lowest gain, or most compression, is applied. The gain is applied by a compressor, and the compressed sound can then be provided to a speaker for a user to hear.

A parallel method to method 500 may take place in another earpiece, such as earpiece 550. Applying the same gain in both the earpiece performing method 500 and earpiece 550 may provide a more natural sound experience for a user of a pair of in-ear hearing protection devices. A more natural sound experience may increase a user's ability to localize sound. Additionally, applying the same gain reduction may reduce feelings of discomfort.

Method 500 may repeat frequently, such that earpiece constantly samples an incoming sound signal and determines an appropriate gain to be applied. In one embodiment, a user's safety is prioritized and a lowest gain is used. For example, if the last time a comparison was conducted a −6 dB gain was the lowest gain, it is used until a new lowest gain is detected. If the earpiece samples again before another received gain 554 is obtained, the new calculated gain is compared to −6 dB, and the lower is again used. This may allow for power savings by reducing the frequency of communication between earpieces.

In another embodiment, both earpieces in a pair of earpieces simultaneously perform method 500, such that both earpieces sample an incoming sound, calculate a gain, and send the calculation simultaneously. The benefit of running method 500 simultaneously in each of a pair of earpieces is that latency is reduced, which improves the naturalness of the sound experience.

In one embodiment, an earpiece is configured to perform method 500 as often as about once per second, or as often as about 5 times per second, or as often as about 10 times per second, or as often as about 20 times per second, or as often as about 50 times per second, or even more frequently.

While the steps of method 500 are described sequentially, in at least some embodiments they may be performed in a different order. For example, in one embodiment, a corresponding gain may be received from another earpiece before a gain is calculated for an earpiece performing method 500.

Embodiments described herein provide systems and methods for using a pair of hearing protection devices to reproduce sound at safe levels for a user. Embodiments described herein require the first and second hearing protection devices to work in concert to produce a more natural sound than would be produced from two hearing protection devices working independently from each other.

In one embodiment, such functionality is achieved by a hard limiter, such that, above a certain sound pressure level, sounds are clipped to a particular threshold. Additionally, the amplifier is disabled when the sound pressure level inside the cup reaches a certain threshold, i.e., the level dependent earpiece amplifier turns off until the sound inside the ear muff falls below the certain threshold.

Figure 6A:
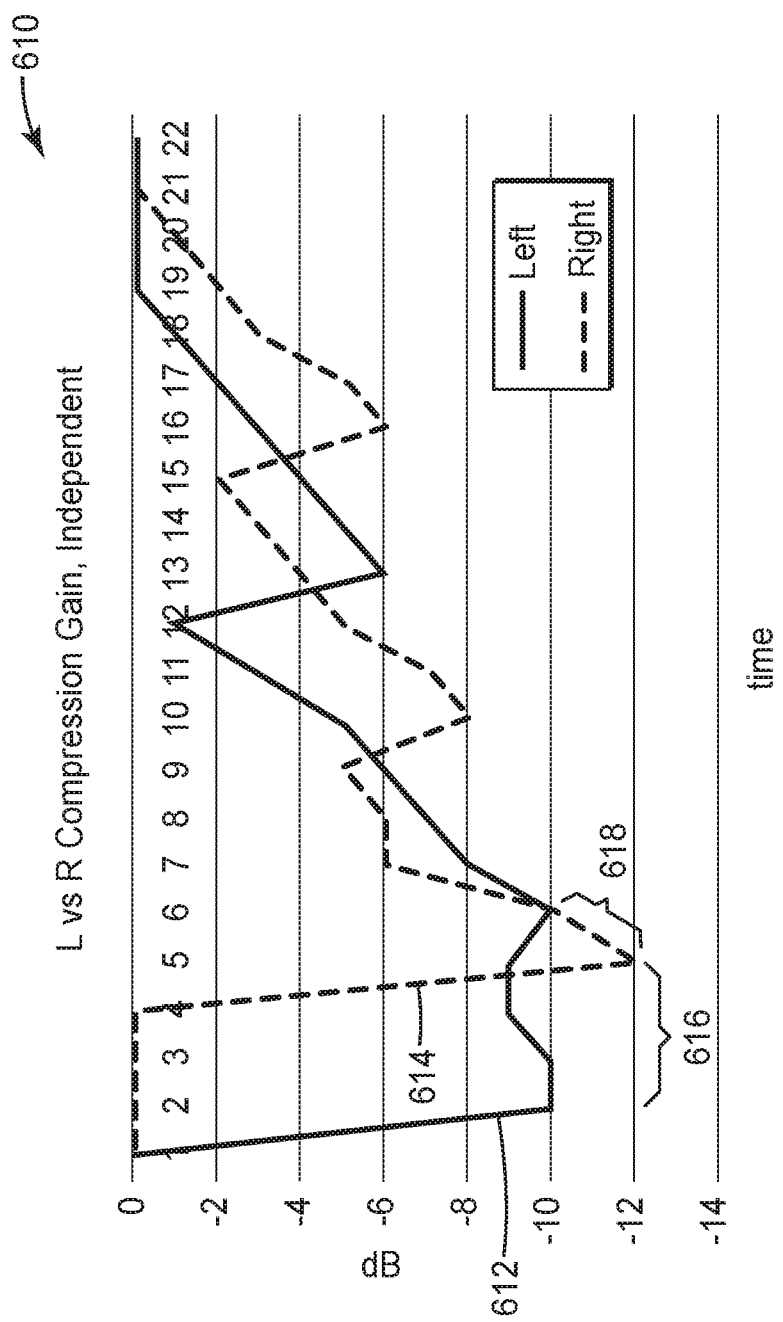
FIGS. 6A and 6B illustrate calculated compression gains for pairs of in-hear hearing protection devices.
Figure 6B:
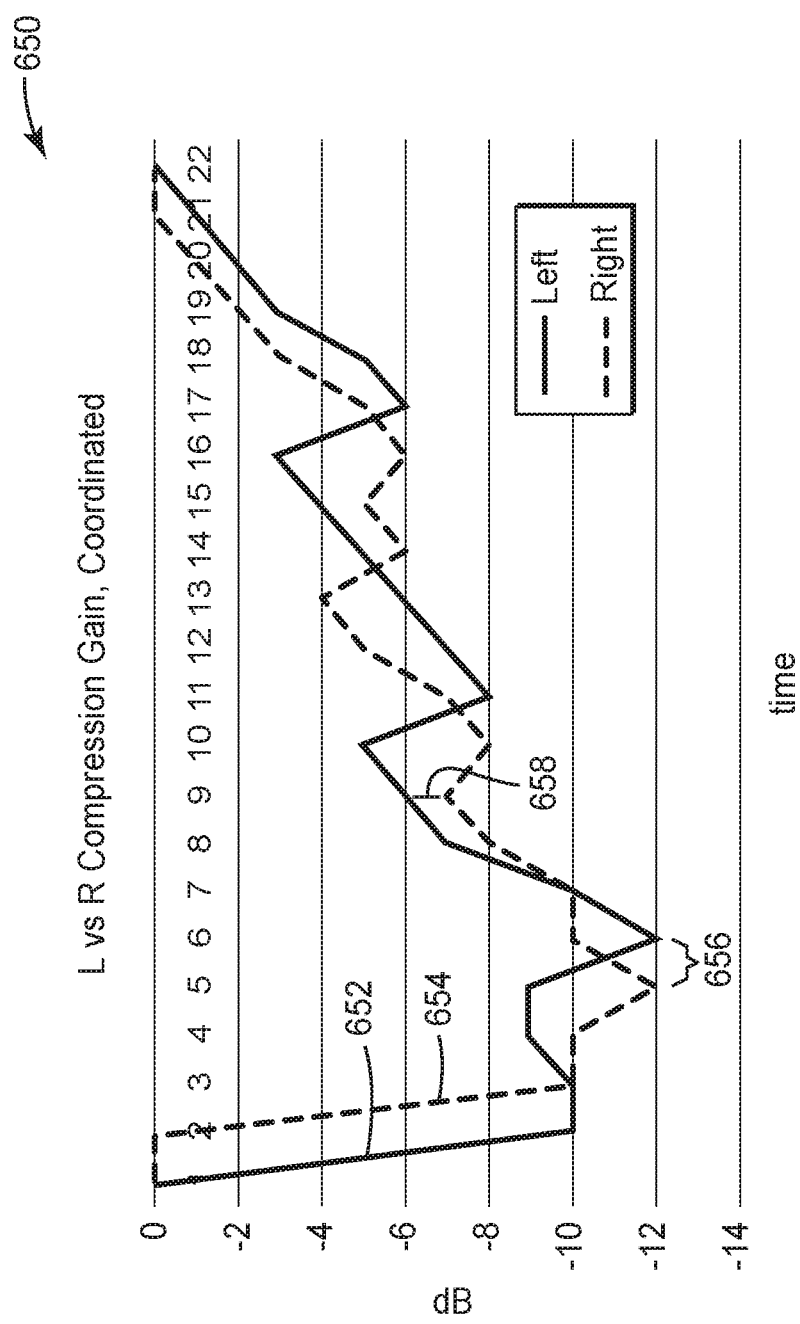

FIGS. 6A and 6B illustrate calculated compression gains for pairs of in-hear hearing protection devices. FIG. 6A illustrates applied gains 610 for a pair of earpieces operating independently. A left earpiece gain 612 and a right earpiece gain 614 illustrate the latency 616 and difference in applied gain 618, that can occur when earpieces operate independently.

FIG. 6B illustrates coordinated gains 650 applied by a pair of earpieces operating according to the systems and/or methods herein. A left earpiece gain 652 and a right earpiece gain 654 are illustrated. As can be seen in the comparison between independent operation 610 and coordinated operation 650, a latency 656 is reduced, as well as a difference in gain applied 658.

An in-ear hearing protection device is presented. The hearing protection device includes a microphone configured to receive an ambient sound. The hearing protection device also includes a processor configured to perform an attenuation function on the received ambient sound to provide an attenuated sound. The hearing protection device also includes a speaker configured to broadcast the attenuated sound. The hearing protection device also includes a communication module configured to receive a second attenuation function detail from a second in-ear protection device. The processor is configured to calculate a first attenuation function detail and compare the first and second attenuation function details. The performed attenuation function is based on one of the first and second attenuation function details.

The in-ear hearing protection device may be implemented such that the first attenuation function detail includes a first gain and, the second attenuation function detail includes a second gain. The performed attenuation function includes a lowest gain between the first and second gain.

The in-ear hearing protection device may be implemented such that the communication module is configured to send the calculated first attenuation function detail to the second in-ear protection device.

The in-ear hearing protection device may be implemented such that the communication module is configured to send the calculated first attenuation function detail to the second in-ear protection device using a wireless network.

The in-ear hearing protection device may be implemented such that the wireless network includes a near-field magnetic induction communication network.

The in-ear hearing protection device may be implemented such that the communication module is configured such that the calculated first attenuation function detail is sent such that it is received by the second in-ear protection device substantially simultaneously as the receipt of the second attenuation function detail by the in-ear protection device.

The in-ear hearing protection device may be implemented such that a controller is configured to manage the near-field magnetic induction communication network.

The in-ear hearing protection device may be implemented such that the first attenuation function detail includes a first equalization parameter and the second attenuation function detail includes a second equalization parameter. The performed attenuation function includes applying one of the first and second equalization parameters.

The in-ear hearing protection device may be implemented such that the first attenuation function detail includes a first volume control parameter, the second attenuation function detail includes a second volume control parameter.

A hearing protection system is presented. The hearing protection system includes a first and second earpiece. Each of the earpieces includes a microphone configured to receive ambient sound and provide the received ambient sound to a processor which performs an attenuation function based on the received ambient sound. Each of the earpieces also includes a speaker configured to broadcast an attenuated sound. Each of the earpieces also includes a communication module configured to send and receive attenuation function data. The first and second earpieces are each configured to operate in a coordinated mode. In the coordinated mode, the first earpiece is configured to: send, using the communication module, a first calculated attenuation function detail to the second earpiece, receive, using the communication module, a second calculated attenuation function detail from the second earpiece, and apply, using the processor one of the first and second calculated attenuation functions to the received ambient sound to produce the attenuated sound.

The hearing protection system may be implemented such that the first calculated attenuation function detail is calculated by a first processor associated with the first earpiece.

The hearing protection system may be implemented such that the second calculated attenuation function detail is calculated by a second processor associated with the second earpiece.

The hearing protection system may be implemented such that the first calculated attenuation function detail is a gain.

E The hearing protection system may be implemented such that the first calculated attenuation function detail is a calculated compression.

The hearing protection system may be implemented such that the first calculated attenuation function detail is an equalization parameter.

The hearing protection system may be implemented such that the first calculated attenuation function detail is a volume control parameter.

The hearing protection system may be implemented such that the first earpiece is configured to send the first calculated attenuation function detail while simultaneously receiving the second calculated attenuation function detail.

The hearing protection system may be implemented such that the first earpiece is configured to repeat the steps of sending, receiving and applying at least once per second.

The hearing protection system may be implemented such that the first earpiece is configured to repeat the steps of sending, receiving and applying at least five times per second.

The hearing protection system may be implemented such that the first earpiece is configured to repeat the steps of sending, receiving and applying at least 10 times per second.

The hearing protection system may be implemented such that the first earpiece is configured to repeat the steps of sending, receiving and applying at least 50 times per second.

The hearing protection system may be implemented such that the first earpiece is configured to directly send the first calculated attenuation function detail to the second earpiece.

The hearing protection system may be implemented such that the first earpiece is configured to send the first calculated attenuation function detail to a controller.

The hearing protection system may be implemented such that the communication module is configured to send and receive data wirelessly.

The hearing protection system may be implemented such that the communication module is configured to operate using near field magnetic induction technology.

The hearing protection system may be implemented such that a latency in the coordinated mode is less than a latency in an independent mode.

A method of coordinating attenuation between a first and second in-ear protection devices is presented. The method includes receiving a sound indication using a microphone of the first in-ear protection device. The method also includes calculating, using a first processor of the first in-ear protection device, a first attenuation parameter value. The method also includes receiving, using a communication module of the first in-ear protection device, a second attenuation parameter value from the second in-ear protection device. The method also includes comparing, using the first processor, the first and second attenuation parameter values. The method also includes applying, using the first processor, one of the first and second attenuation parameter values to a sound signal.

The method may be implemented such that it also includes broadcasting an attenuated sound signal through a speaker of the in-ear protection device.

The method may be implemented such that the first in-ear protection device calculates the first attenuation parameter value at least once per second.

The method may be implemented such that the first in-ear protection device receives the second attenuation parameter value at least once per second.

The method may be implemented such that it also includes receiving a second sound indication using a second microphone of the second in-ear protection device. The method also includes calculating, using a second processor of the second in-ear protection device, the second attenuation parameter value. The method also includes receiving, using a second communication module of the second in-ear protection device, the first attenuation parameter value from the first in-ear protection device. The method also includes comparing, using the second processor, the first and second attenuation parameter values. The method also includes applying, using the second processor, one of the first and second attenuation parameter values to a second sound signal.

The method may be implemented such that the first and second processor apply the same attenuation parameter value.

The method may be implemented such that the steps of receiving the first attenuation parameter value and receiving the second attenuation parameter value occur substantially simultaneously.

The method may be implemented such that it also includes applying, using a second processor of the second in-ear protection device, one of the first and second attenuation parameter values to a sound signal.

The method may be implemented such that the first and second processors apply the same attenuation parameter value.

The method may be implemented such that the second attenuation parameter value is received from the second in-ear protection device.

The method may be implemented such that the second attenuation parameter value is received from a controller.

The method may be implemented such that the communication module and the second communication module are configured to communicate wirelessly.

The method may be implemented such that the communication module is configured to communicate using NFMI.

The method may be implemented such that the communication module is also configured to communicate the sound signal wirelessly.

EXAMPLES

Example 1

Figure 7B:
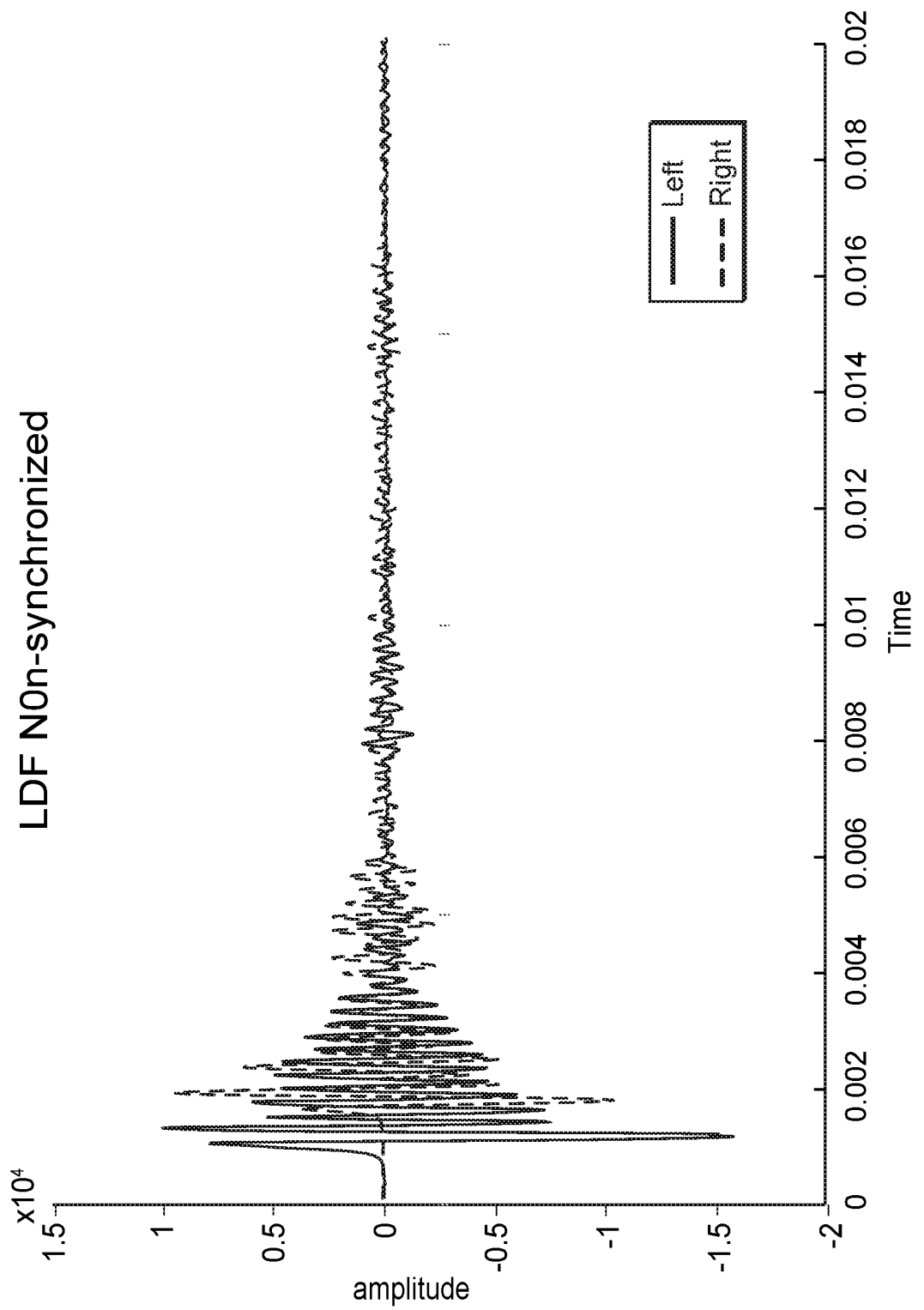

FIG. 7A illustrates the sound measured at the Left and Right Ears of a Kemar Acoustic Test Mannequin, with no hearing protector in place.

Notice the higher amplitude of the left signal compared to the right due to the sound emanating from the left side. This interaural level difference (ILD) is an important directional cue for the brain.

Note there is also approximately 1 ms delay before the sound reaches the right ear. This delay is know as interaural time difference (ITD).

Example 2

This is the sound measured at the Left and Right Ears of the same Kemar mannequin as Example 1, with original "non-synchronized" in-ear hearing protectors installed. Notice the left signal has been significantly attenuated by the sound compression (LDF) function, however the right signal has not been affected as it is much lower in amplitude. The end result is the interaural level difference (ILD) has been significantly disturbed, making it more difficult to localize sound.

Example 3

This is the sound measured at the Left and Right Ears of the same Kemar mannequin as in Examples 1 and 2, with the "synchronized" in-ear hearing protectors installed. Notice the left signal has been significantly attenuated to a safe listening level by the sound compression (LDF) function, and in this case the right signal has been attenuated as well due to the coordination of the devices. The end result is the interaural level difference (ILD) has been preserved, which allows for more effective sound localization.

What is claimed is:
1. An in-ear hearing protection device comprising:
a microphone configured to receive an ambient sound;

a processor configured to perform an attenuation function on the received ambient sound to provide an attenuated sound;

a speaker configured to broadcast the attenuated sound;

a receiver configured to wirelessly receive a second attenuation function detail from a second in-ear protection device, wherein the processor is configured to calculate a first attenuation function detail, compare the first and second attenuation function details, and wherein the performed attenuation function is based on one of the first and second attenuation function details, wherein the first attenuation function detail comprises a first gain, the second attenuation function detail comprises a second gain, and wherein the performed attenuation function comprises a lowest gain between the first and second gain;

wherein the performed attenuation function is based on the lowest gain between the first and second attenuation function details;

wherein the in-ear hearing protection device is configured to receive second attenuation function details at least once per second; and wherein the processor is configured to apply a level dependent attenuation function to a received ambient sound.

2. The in-ear hearing protection device of claim 1, wherein a communication module is configured to send the calculated first attenuation function detail to the second in-ear protection device.

3. The in-ear hearing protection device of claim 1, wherein the first attenuation function detail comprises a first equalization parameter, the second attenuation function detail comprises a second equalization parameter, and wherein the performed attenuation function comprises applying one of the first and second equalization parameters.

4. A hearing protection system comprising:

a first and second earpiece, each of the first and second earpieces comprising:

a microphone configured to receive ambient sound and provide the received ambient sound to a processor which performs an attenuation function based on the received ambient sound;

a speaker configured to broadcast an attenuated sound;

a communication module configured to send and receive attenuation function data;

wherein both the first and second earpieces are active hearing protection devices; and wherein the first and second earpieces are each configured to operate in a coordinated mode, and wherein in the coordinated mode the hearing protection system is configured to:

send, from the first earpiece to the second earpiece, using the communication module, a first calculated attenuation function detail to the second earpiece and send, from the second earpiece to the first earpiece, using the communication module, a second calculated attenuation function detail to the first earpiece, and wherein each of the first and second calculated attention function details comprises a gain;

receive wirelessly, at the first earpiece, the second calculated attenuation function detail from the second earpiece and receive, at the second earpiece, wirelessly, the first calculated attention function detail from the first earpiece; and apply, at both the first and second earpieces, using the processor, one of the first and second calculated attenuation functions to the received ambient sound to produce the attenuated sound, wherein the applied calculated attenuation function comprises the lowest gain of the first and second calculated attenuation function details; and wherein the first or second earpiece is configured to perform operations of the coordinated mode at least once per second.

5. The system of claim 4, wherein the first calculated attenuation function detail is calculated by a first processor associated with the first earpiece and the second calculated attenuation function detail is calculated by a second processor associated with the second earpiece.

6. The system of claim 4, wherein the first calculated attenuation function detail comprises:

a calculated compression, an equalization parameter, or a volume control parameter.

7. The system of claim 4, wherein the first earpiece is configured to send the first calculated attenuation function detail while simultaneously receiving the second calculated attenuation function detail.

8. The system of claim 4, wherein the first earpiece is configured to repeat the steps of sending, receiving and applying at least once per second.

9. The system of claim 4, wherein the first earpiece is configured to directly send the first calculated attenuation function detail to the second earpiece.

10. The system of claim 4, wherein the first earpiece is configured to send the first calculated attenuation function detail to a controller.

11. The system of claim 4, wherein the communication module is configured to operate using near field magnetic induction technology.

12. The system of claim 4, wherein a latency in the coordinated mode is less than a latency in an independent mode.

13. A method of coordinating attenuation between a first and second in-ear protection devices, the method comprising:

receiving a sound indication using a microphone of the first in-ear protection device;

calculating, using a first processor of the first in-ear protection device, a first attenuation function detail, the first attenuation function detail comprising, a first gain;

receiving, at the first in-ear protection device, a second attenuation function detail, comprising a second gain, from the second in-ear protection device;

comparing, using the first processor, the first and second attenuation function details; and applying, using the first processor, the lowest of the first and second gains; and wherein both the first and second in-ear protection devices are active hearing protection devices, wherein the method is performed at least once per second in the first or second in-ear protection device.

14. The method of claim 13, and further comprising broadcasting an attenuated sound signal through a speaker of the in-ear protection device.

15. The method of claim 13, and also comprising the steps of:

receiving a second sound indication using a second microphone of the second in-ear protection device;

calculating, using a second processor of the second in-ear protection device, the second attenuation function detail, the second attenuation function detail comprising the second gain;

receiving, using a second communication module of the second in-ear protection device, the first attenuation function detail from the first in-ear protection device;

comparing, using the second processor, the first and second attenuation function details; and applying, using the second processor, the lowest of the first and second gains.

16. The method of claim 13, wherein the second attenuation parameter value is received from the second in-ear protection device.

17. The method of claim 13, wherein the second attenuation parameter value is received from a controller.

* * * * *